US012721853B2

(12) United States Patent
Chen et al.

(10) Patent No.: US 12,721,853 B2
(45) Date of Patent: Sep. 1, 2026

(54) APPLICATIONS OF CX-5461 IN TREATING IMMUNE REJECTION IN RENAL TRANSPLANTATION

(71) Applicants: Sun Yat-sen University, Guangzhou (CN); The First Affiliated Hospital, Sun Yat-sen University, Guangzhou (CN)

(72) Inventors: Hongbo Chen, Guangzhou (CN); Peilin Shi, Guangzhou (CN); Fang Cheng, Guangzhou (CN); Longshan Liu, Guangzhou (CN); Changxi Wang, Guangzhou (CN); Zirong Bi, Guangzhou (CN)

(73) Assignees: SUN YAT-SEN UNIVERSITY, Guangzhou (CN); THE FIRST AFFILIATED HOSPITAL, SUN YAT-SEN UNIVERSITY, Guangzhou (CN)

( * ) Notice: Subject to any disclaimer, the term of this patent is extended or adjusted under 35 U.S.C. 154(b) by 272 days.

(21) Appl. No.: 18/761,482

(22) Filed: Jul. 2, 2024

(65) Prior Publication Data

US 2024/0350513 A1 Oct. 24, 2024

Related U.S. Application Data

(63) Continuation of application No. PCT/CN2023/091648, filed on Apr. 28, 2023.

(30) Foreign Application Priority Data

May 12, 2022 (CN) ........................ 202210514892.1

(51) Int. Cl.
*A61K 31/551* (2006.01)
*A61P 37/06* (2006.01)

(52) U.S. Cl.
CPC ........... *A61K 31/551* (2013.01); *A61P 37/06* (2018.01)

(58) Field of Classification Search
CPC ............................ A61K 31/551; A61P 37/06
See application file for complete search history.

(56) References Cited

U.S. PATENT DOCUMENTS 10,022,382 B2 * 7/2018 Achiron .............. C12Q 1/6876

FOREIGN PATENT DOCUMENTS

| | | | |
|---|---|---|---|
| CN | 108904508 | A | 11/2018 |
| CN | 109251970 | A | 1/2019 |
| CN | 112121142 | A | 12/2020 |
| CN | 113521080 | A | 10/2021 |
| CN | 114652729 | A | 6/2022 |

OTHER PUBLICATIONS

Hsiang-i Tsai et al., "NF45/NF90-mediated rDNA transcription provides a novel target for immunosuppressant development," EMBO Molecular Medicine, vol. 13, No. e12834, Feb. 8, 2021 (Feb. 8, 2021), pp. 1-18.
Denis Drgin, et al., "Targeting RNA polymerase I with an oral small molecule CX-5461 inhibits ribosomal RNA synthesis and solid tumor growth," Cancer Research, vol. 71, No. 4. Feb. 15, 2011 (Feb. 28, 2011), pp. 1418-1430.
International Search Report issued in corresponding PCT Application No. PCT/CN2023/091648, dated Jul. 26, 2023 (Jul. 26, 2023).
SIPO office action dated Jan. 6, 2023 (Jan. 6, 2023) in application 202210514892.1.

* cited by examiner

*Primary Examiner* — Kamal A Saeed
(74) *Attorney, Agent, or Firm* — Pilloff Passino & Cosenza LLP; Rachel Pilloff; Sean Passino

(57) ABSTRACT

Applications of CX-5461 in preparing a medicine for treating renal transplant immune rejection and a medicine for treating immune rejection after renal transplantation are provided in the present disclosure. CX-5461 significantly reduces immune rejection in renal transplantation, and is used as a new immunosuppressant to treat renal allograft rejection, especially the acute rejection after renal transplantation.

1 Claim, 16 Drawing Sheets

Specification includes a Sequence Listing.

SEQUENCE LISTING

```
Sequence total quantity: 8
SEQ ID NO: 1            moltype = DNA  length = 20
FEATURE                 Location/Qualifiers
source                  1..20
                        mol_type = other DNA
                        organism = synthetic construct
SEQUENCE: 1
cattccatcc ggggtgacaa                                      20

SEQ ID NO: 2            moltype = DNA  length = 20
FEATURE                 Location/Qualifiers
source                  1..20
                        mol_type = other DNA
                        organism = synthetic construct
```

-continued

```
SEQUENCE: 2
gtagatgccg ggtggttcaa                                              20

SEQ ID NO: 3            moltype = DNA  length = 20
FEATURE                 Location/Qualifiers
source                  1..20
                        mol_type = other DNA
                        organism = synthetic construct
SEQUENCE: 3
gtgaaggcag cggtactcat                                              20

SEQ ID NO: 4            moltype = DNA  length = 20
FEATURE                 Location/Qualifiers
source                  1..20
                        mol_type = other DNA
                        organism = synthetic construct
SEQUENCE: 4
atgtggtggt ccaacttccc                                              20

SEQ ID NO: 5            moltype = DNA  length = 19
FEATURE                 Location/Qualifiers
source                  1..19
                        mol_type = other DNA
                        organism = synthetic construct
SEQUENCE: 5
aactcccatt cttccacct                                               19

SEQ ID NO: 6            moltype = DNA  length = 21
FEATURE                 Location/Qualifiers
source                  1..21
                        mol_type = other DNA
                        organism = synthetic construct
SEQUENCE: 6
ttgtcatacc aggaaatgag c                                            21

SEQ ID NO: 7            moltype = DNA  length = 20
FEATURE                 Location/Qualifiers
source                  1..20
                        mol_type = other DNA
                        organism = synthetic construct
SEQUENCE: 7
agagacttcc agccagttgc                                              20

SEQ ID NO: 8            moltype = DNA  length = 20
FEATURE                 Location/Qualifiers
source                  1..20
                        mol_type = other DNA
                        organism = synthetic construct
SEQUENCE: 8
agtctcctct ccggacttgt                                              20
```

APPLICATIONS OF CX-5461 IN TREATING IMMUNE REJECTION IN RENAL TRANSPLANTATION

CROSS-REFERENCE TO RELATED APPLICATIONS

This application is a continuation of PCT/CN2023/091648, filed Apr. 28, 2023 and claims priority of Chinese Patent Application No. 202210514892.1, filed on May 12, 2022, the entire contents of which are incorporated herein by reference.

INCORPORATION BY REFERENCE STATEMENT

This statement, made under Rules 77 (b) (5) (ii) and any other applicable rule incorporates into the present specification of an XML file for a "Sequence Listing XML" (see Rule 831 (a)), submitted via the USPTO patent electronic filing system or on one or more read-only optical discs (see Rule 1.52 (e) (8)), identifying the names of each file, the date of creation of each file, and the size of each file in bytes as follows:

File name: 347-220-0956-sequence
Creation date: Wednesday, Jun. 26, 2024
Byte size: 8,268

TECHNICAL FIELD

The present disclosure relates to the technical field of biomedicine, and in particular to applications of CX-5461 in treating immune rejection in renal transplantation.

BACKGROUND

Kidney transplantation has become one of the main treatments for patients with end-stage renal disease. However, immune rejection caused by allogeneic organs seriously affects the life span of the transplanted organ, making transplantation immune rejection an urgent clinical problem to be solved at present. The survival of transplanted kidney is affected by many factors, which are mainly divided into factors of pre-transplantation and factors of post-transplantation, with pre-transplantation factors basically including brain death and organ ischaemia time, and post-transplantation factors mainly involving reperfusion injury, infection, rejection, nephrotoxicity and so on. Among them, acute rejection is the most frequently reported complication after renal transplantation.

The mechanism of acute rejection, one of the most common type of rejection after kidney transplantation, is mainly the cellular immune response. With the wide application of human leukocyte antigen (HLA) gene-matching technology and the continuous development of new immunosuppressive drugs of high efficiency and low toxicity, the success rate of renal transplantation has improved greatly in recent, yet there is still a certain incidence of postoperative acute rejection. Moreover, acute rejection is an important risk factor leading to the loss of implant in the long term. An early prevention or suppression of acute rejection in the postoperative period is of great significance for early treatment and for improving the long-term survival rate of postoperative implant.

Cyclosporine was introduced to organ transplantation after the year of 1987, bringing about a breakthrough in the clinical outcomes of various organ transplants. However, with the further development of research and the accumulation of clinical experience, it has been shown that cyclosporine, while exerting its immunosuppressive effect, may produce toxicity to the kidneys and lead to renal fibrosis, as well as causing metabolic abnormalities such as hyperlipidaemia, hypertension, hyperglycemia and hyperuricaemia. All these side effects may result in reduced function of the transplanted kidney, thus affecting the long-term function of the transplanted kidney and the survival of the recipient. Therefore, drugs that are capable of treating post-transplantation immune rejection, reducing the activity of the immune system, significantly inhibiting the occurrence of acute post-transplantation rejection with fewer toxic side effects and prolonging the survival of the implant are required.

CX-5461 is an rRNA synthesis inhibitor that selectively inhibits Pol I-driven rRNA transcription with an $IC_{50}$ of 142 nM in HCT-116, A375, and MIA PaCa-2 cells; it has no effect on Pol II, and inhibits rRNA transcription 250- to 300-fold more selectively than it inhibits DNA replication and protein translation. Chinese patent CN108904508A discloses an application of CX-5461 in preparing an agent for inhibiting skin allograft rejection. However, there is no report on the effect of CX-5461 on immune rejection of renal transplantation, especially on acute rejection after renal transplantation and on renal ischemia-reperfusion injury after renal transplantation.

SUMMARY

The present disclosure aims at overcoming the above defects and deficiencies in the prior art, and providing new applications of CX-5461 in preparing drugs for treating renal transplant immune rejection.

The above objectives of the present disclosure are achieved by the following technical scheme.

According to the study of the present disclosure, CX-5461 is proved to be capable of significantly reducing the occurrence of acute rejection of renal transplantation and resisting renal ischaemia-reperfusion injury after renal transplantation. Through hematoxylin and cosin (H&E) stains and immunohistochemistry, it is found that CX-5461-treated transplants show reduced fibrosis and reduced immune infiltration, reduced creatinine and urea nitrogen levels in the blood of rats after renal transplantation, reduced levels of IL-17A cytokines in renal transplants and pro-inflammatory IL-6 cytokines in vivo, etc., and elevated proportions of Treg cells in the spleen and levels of anti-inflammatory cytokine IL-10, extended survival of rats, reduced creatinine levels in the blood and significantly prolonged long-term survival of rats after renal transplantation, indicating that CX-5461 is capable of being used as a novel immunosuppressant for the treatment of immune rejection, especially for the treatment of immune rejection in rats, with protective effect against post-transplant renal ischaemia-reperfusion injury.

Accordingly, the present disclosure requests protection of CX-5461 in the following applications:

- an application of CX-5461 in preparing drugs for treating immune rejection after renal transplantation;
- an application of CX-5461 in preparing drugs for inhibiting acute rejection after renal transplantation;
- an application of CX-5461 in preparing protective preparation against renal ischemia-reperfusion injury after renal transplantation;
- an application of CX-5461 in preparing drugs for reducing creatinine and urea nitrogen levels in blood of patients after renal transplantation;

- an application of CX-5461 in preparing drugs for reducing inflammatory cytokines in renal implants after renal transplantation and inflammatory cytokine levels in patients after renal transplantation;
- an application of CX-5461 in preparing drugs for improving anti-inflammatory cytokines in renal implants after renal transplantation and proportion of Treg cells and levels of anti-inflammatory cytokines in patients after renal transplantation;
- an application of CX-5461 in preparing drugs for reducing fibrosis level of renal implants and lowering immune infiltration degree after renal transplantation.

Optionally, the inflammatory cytokines include IL-6 and/or IL-17A.

Optionally, the anti-inflammatory cytokines include IL-10.

The present disclosure also provides a medicine for accurately treating immune rejection after renal transplantation, where the medicine takes CX-5461 as a main active ingredient, with capability of inhibiting acute rejection reaction after renal transplantation, reducing creatinine and urea nitrogen after renal transplantation, lowering levels of IL-17A cytokines in rat renal implants and pro-inflammatory IL-6 cytokines in vivo, etc., and elevating proportion of Treg cells in vivo and level of anti-inflammatory cytokine IL-10 in vivo, and significantly prolonging long-term survival rate after renal transplantation.

Optionally, the medicine also includes a medicine for treating immune rejection after renal transplantation in cooperation with CX5461.

Optionally, the medicine further includes a pharmaceutically acceptable carrier and/or excipient.

Optionally, forms of the medicine include, but are not limited to, oral liquid, granules, capsule, tablet, particle, pilula, ointment and injection.

Compared with the prior art, the present disclosure has the following beneficial effects.

The present disclosure provides new applications of CX-5461 in preparing drugs for treating renal transplant immune rejection. According to the research of the present disclosure, CX-5461 is capable of obviously reducing the occurrence of acute rejection of renal transplantation and resisting renal ischemia-reperfusion injury after renal transplantation; specifically, CX-5461 is effective in reducing the fibrosis degree and immune infiltration degree of renal transplantation, reducing the levels of creatinine and urea nitrogen in the blood of rats after renal transplantation, and reducing the levels of IL-17A cytokines in rat renal transplantation and IL-6 cytokines in vivo. It is also effective in increasing the proportion of Treg cells in spleen and the level of anti-inflammatory cytokine IL-10, prolonging the survival period of rats and significantly prolonging the long-term survival rate after renal transplantation, suggesting that CX-5461 may be used as a new immunosuppressant to treat renal transplantation immune rejection, especially to inhibit acute rejection after renal transplantation. Furthermore, CX-5461 is capable of reducing post-transplant renal ischaemia-reperfusion injury.

DETAILED DESCRIPTION OF THE EMBODIMENTS

Figure 1:
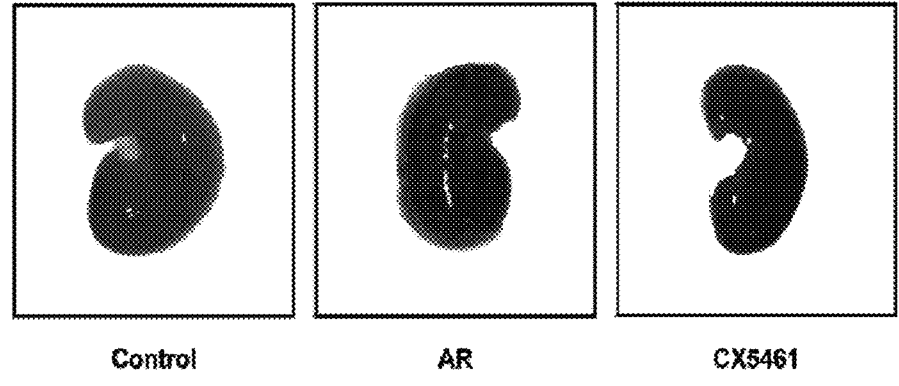
FIG. 1 shows the appearance of the renal implants on the seventh day after CX-5461-treated renal transplantation, which reveals a reduction of renal fibrosis without significant inflammatory immune infiltration in CX-5461-treated kidneys.

The present disclosure is further explained with reference to the attached drawings in the specification and specific embodiments, but the embodiments do not limit the present disclosure in any form. Unless otherwise specified, the reagents, methods and equipment used in the present disclosure are conventional reagents, methods and equipment in the technical field.

Unless otherwise specified, the reagents and materials used in the following embodiments are all commercially available.

The structural formula of CX-5461 is shown below, and the CX-5461 is purchased from Shanghai Biochem Safebuy Technology Co., Ltd.

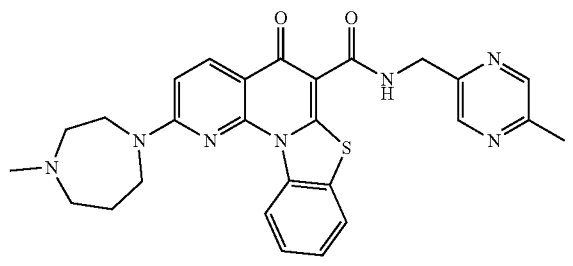

Embodiment 1 Effect of CX-5461 on Immune Rejection after Renal Transplantation in Rats

1. Experimental Method (1) Lewis male rats and Brown Norway male rats are purchased from Beijing Vital River Laboratory Animal Technology Co., Ltd., with weight of around 200 g and age of 6-8 weeks old, and the rearing environment is of SPF level.

(2) Establishment of acute rejection model after renal transplantation in rats: the donor of Brown Norway male rats aged 6-8 weeks, about 200 g, is transplanted into Lewis male rats, and the surgical scheme is end-to-end renal vein anastomosis as reported in most literatures. The experimental groups are divided into normal group (Control) of donor rats, acute rejection (AR) group and drug group (CX5461 of 2 mg/kg) with 5 rats each. After successful renal transplantation, the rats are killed at 3 days, 5 days and 7 days after operation, and blood is collected from the lower abdominal aorta by using a 5 mL sterile syringe. The collected blood is placed in a procoagulants tube at room temperature for 1 h, centrifuged at 4000 r/min in a centrifuge at 4° C. for 10 min, and the obtained serum is packaged in an EP tube and frozen at −80° C. for enzyme-linked immunosorbent assay (ELISA) detection. The removed transplanted kidney is cut in half along the longitudinal axis and soaked in 4% paraformaldehyde for pathological reaction verification.

(3) Real-time RT-PCR analysis: RNA is extracted from rat spleen by using Trizol method, and the specific operation is as follows: 1 mL of Trizol is added to the EP tube containing rat spleen and placed in the refrigerator at 4° C. for 10 min; then, porcelain beads are added into it and put into an automatic grinder, and ground at 4° C. for 5 min; 0.2 mL chloroform (i.e., ⅕ Trizol volume) is added into the EP tube, followed by shaking vigorously for about 20 times, then centrifuging at 12,500 rpm at 4° C. for 15 min; the obtained upper aqueous phase is placed in a new EP tube and carefully aspirated about 3 times with a 200 μL gun tip, and approximately an equal volume of isopropanol (i.e., 600 μL) is added, and the RNA is precipitated by centrifugation at 12,500 rpm for 15 min at 4° C., at which time a white RNA precipitate is seen. Then, 1 ml of 75% ethanol is added for washing twice, followed by centrifugation at 12500 rpm and 4° C. for 5 min. The supernatant is discarded and the precipitated RNA is allowed to dry naturally in an ultra-clean bench. RNA is obtained by dissolving the RNA precipitate with 100 μL of Rnase-free water. Subsequently, the concentration and purity of total RNA are measured using a Nanodrop. Using the RNA as a template, reverse transcription is performed by reverse transcription kit of Beijing TransGen Biotech Company to obtain a cDNA template, and quantitative PCR analysis is carried out by using this cDNA as a template and using TransGen qPCR kit according to the instructions and the detection primers shown in Table 1 below.

TABLE 1

Sequence details of primers used in the experiment

| Primer name | Primer sequence (5'-3') |
|---|---|
| IL-10 Forward | CATTCCATCCGGGGTGACAA (SEQ ID NO. 1) |
| IL-10 Reverse | GTAGATGCCGGGTGGTTCAA (SEQ ID NO. 2) |
| IL-17A Forward | GTGAAGGCAGCGGTACTCAT (SEQ ID NO. 3) |
| IL-17A Reverse | ATGTGGTGGTCCAACTTCCC (SEQ ID NO. 4) |
| GAPDH Forward | AACTCCCATTCTTCCACCT (SEQ ID NO. 5) |
| GAPDH Reverse | TTGTCATACCAGGAAATGAGC (SEQ ID NO. 6) |
| IL-6 Forward | AGAGACTTCCAGCCAGTTGC (SEQ ID NO. 7) |
| IL-6 Reverse | AGTCTCCTCTCCGGACTTGT (SEQ ID NO. 8) |

(4) ELISA: the operation shall be carried out according to the instructions of Dakewe reagent kit. Before use, all reagents shall be fully mixed to avoid foaming. Sample addition: diluted cytokine standard is added to the well of standard at 100 μL/well, the sample is added to the well of standard at 100 μL/well, and dilution buffer (1×) is added into the well of blank control at 100 μL/well.

Detection antibody addition: biotinylated antibody working solution is added at 50 μL/well, and incubated at 37° C. for 90 min. Board washing: washing buffer working solution of 300 μL/Well is used for washing for 1 min and discarded, with repetition for three times. Enzyme addition: streptavidin-HRP working solution is added at 100 μL/well and incubated at 37° C. for 30 min. After repeating the plate-washing operation, each well is added with 100 μL of TMB chromogenic solution and incubated for 20 min at 37° C. away from light. Finally, the reaction is rapidly terminated by adding stop solution at 100 μL/well.

OD value of standard or specimen=OD450 value of standard or specimen-OD450 value of blank hole. Standard curve: the concentration of the standard is used as the horizontal coordinate, the OD value is used as the vertical coordinate, and a smooth line is used to connect the coordinate points of each standard. The concentration of a specimen may be found on the standard curve by its OD value.

(5) H&E staining:

1) fixation: the removed kidney tissues are washed using saline, followed by fixation in 4% paraformaldehyde for 24 h, and then rinsed twice with running water for 30 min each time;

2) dehydration and transparency: kidney tissues are sequentially immersed in graded alcohol (70%, 80%, 90%, 95%, 100%) for 20 min, followed by immersion in a mixture of ethanol:xylene (1:1) for 20 min, and then the kidney tissues are placed in xylene I, xylene II, and xylene III solutions sequentially for 40 min, until the tissues are observed to be transparent;

3) wax soaking and embedding: the soaked kidney tissues are transferred to paraffin wax and soaked for 3 times, 2 h each time;

4) patching and slicing: the embedded block is taken out, and the paraffin-embedded block is sliced at a thickness of 5 μm, and immediately transferred to a warm water bath, and then pasted onto slides after the slices are completely spread out, then the slides are placed in a constant temperature box at 55° C. for drying, and the produced paraffin slices of kidney tissues are placed and stored at normal temperature;

5) dewaxing: the paraffin slices of kidney tissues are soaked in xylene for 3 times, each time for 10 min;

6) hydration of gradient alcohol: the paraffin slices are placed in gradient alcohol (100%, 100%, 95%, 90%, 80%, 70% and 50%) and soaked for 5 min in turn;

7) dyeing and differentiation: the dehydrated slices are stained by immersing them in hematoxylin for 10 min, then the slices are taken out and the hematoxylin staining solution is gently shaken off, followed by rinsing with distilled water to remove the residual staining solution; then the slices are differentiated in 1% hydrochloric acid for 2 s;

8) staining: the tissue slices are rinsed with distilled water and then sequentially immersed in alcohol (50%, 70%, 80%) and eosin staining solution for 2 min each time;

9) dehydration and transparency: the tissue slices after staining are dehydrated and the kidney tissue slices are sequentially immersed in graded alcohol (80%, 90%, 95%, 100%, 100%) for 2 min, followed by placing them in xylene until they are transparent;

10) slice sealing: neutral resin is dropped onto the tissue slices, which are covered with a coverslip and placed in a fume hood; and 11) pathological picture shooting: the tissue slices are placed under an optical microscope for observation and pictures are taken for preservation.

(6) Immunohistochemistry:

1) dewaxing: the paraffin slices of kidney tissues are soaked in xylene for 3 times, each time for 10 min;

2) hydration with gradient alcohol: paraffin slices are immersed in graded alcohol (100%, 100%, 95%, 90%, 80%, 70%, 50%) for 5 min sequentially;

3) antigen repair: the kidney tissue slices are placed into 0.01 mol/L citrate buffer, then wrapped by tin foil paper and placed in a microwave oven, followed by heating for 20 min under medium fire; the kidney tissue slices are taken out and cooled at room temperature, followed by rinsing with PBS for three times, each time for 5 min;

4) enzyme activity elimination: an oil-based pen is used to draw circles along the tissue, the slides are placed in a wet box, the slides are added with drops of 3% $H_2O_2$—PBS solution and incubated for 30 min at room temperature, then rinsed three times with distilled water;

5) sealing: excess water is wiped off the slide, a circle is drawn along the tissue with an oil-based pen, and the slide is placed in a wet box with drops of sealing solution and incubated for 30 min at 37° C. in an oven;

6) incubation of primary antibody: after sealing, the slides are taken out and the excess scaling solution is wiped off with absorbent paper, the slides are placed in a wet box, and the prepared primary antibody (anti-IL-17A) is added dropwise on the slices so that the tissues are completely covered, and then the wet box is placed in the refrigerator at 4° C. overnight; the next day, the wet box is removed from the refrigerator and incubated at room temperature for 1 h; the slides are taken out and the primary antibody is removed, and washed three times with PBS for 5 min each time;

7) incubation of secondary antibody: the liquid on the slides is absorbed with absorbent paper, and then appropriate amount of biotin-labelled secondary antibody is added dropwise on the slices to cover the tissues completely, and incubated at 37° C. for 40 min; when the incubation is finished, the secondary antibody is removed, and then washed with PBS three times, each time for 5 min;

8) DAB development: an appropriate amount of freshly prepared DAB chromogenic solution is added to the slide so that the tissue is completely covered, and the staining is carried out for 5-10 min at room temperature, protected from light, and the slices are placed under the microscope to observe the colour development, and the staining is terminated by placing them in water as soon as the DAB colour is developed;

9) re-staining and differentiation: an appropriate amount of hematoxylin is added dropwise to the slices to completely cover the tissue, staining is carried out for 3 min, then the hematoxylin stain is removed, followed by rinsing with distilled water to remove any residual staining, and then the slices are differentiated in 1% hydrochloric acid for 2 s;

10) bluing: the tissues are placed in PBS and for bluing for 30 s;

11) dehydration and transparency: the tissue slices are placed into gradient alcohol (50%, 70%, 80%, 90%, 95%, 100%, 100%) in turn, and soaked for 5 min each, followed by soaking in in xylene until transparent;

12) slice sealing: neutral resin is dropped onto the tissue slices, which are covered with a coverslip and placed in a fume hood;

13) pathological picture shooting: the tissue slices are placed under an optical microscope for observation and pictures are taken for preservation.

(7) $CD4^+CD25^+Foxp3^+$ flow cytometry: the spleen is ground into a single cell suspension with a grinding screen. 100 μL of spleen cell suspension is taken, firstly, 1 μL of flow antibody CD4 and CD25 is added for staining, after that, 1 mL of fixation solution is added for fixation, after removing the fixation solution, membrane permeabiliser is added, the reaction is washed and resuspended in PBS after 30 min, and then 1 μL of Foxp3 antibody is added (at the same time, a homotypic control reaction tube is set up), the reaction is washed after 30 min, then the reaction is resuspended in 200 μL of PBS, and the percentage of Treg cells in the spleen is detected by flow cytometry.

Statistical methodology: all the experiments are repeated at least three times, and the results are expressed as the average±SD. The statistical significance of all the results is determined by the t test of GraphPad Prism 8, where $p<0.05$ is considered statistically significant. *$P<0.05$; $P<0.01$; *$P<0.001$.

2. Experimental Results

On the seventh day after renal transplantation, the appearance of the kidney graft is shown in FIG. 1. Compared with acute rejection group (AR), the kidney treated with CX-5461 has less renal fibrosis and no obvious inflammatory immune infiltration, suggesting that CX-5461 is capable of reducing ischemia-reperfusion injury and immune inflammatory reaction after renal transplantation.

Figure 2A:
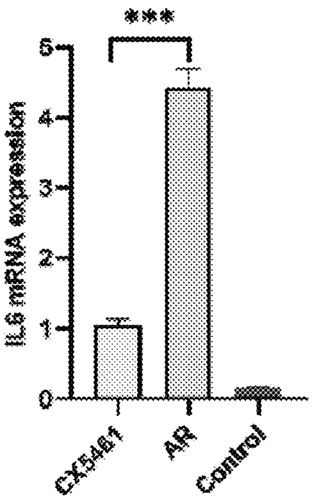
FIG. 2A shows the effect of CX-5461 on IL-6 cytokine in spleen on the seventh day after renal transplantation.
Figure 2B:
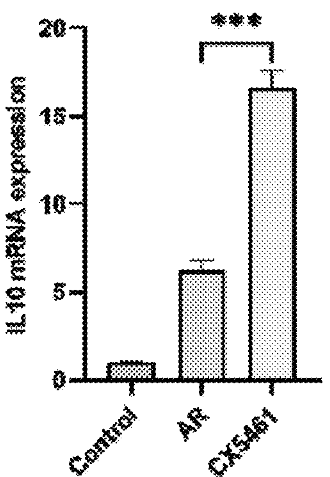
FIG. 2B shows the effect of CX-5461 on IL-10 cytokine in spleen on the seventh day after renal transplantation.
Figure 2C:
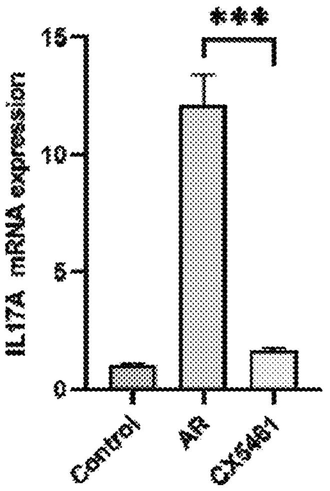
FIG. 2C shows the effect of CX-5461 on IL-17a cytokine in spleen on the seventh day after renal transplantation.

On the seventh day after renal transplantation, the results of related cytokines in the spleen are shown in FIG. 2A-FIG. 2C. It is found that the IL-6 and IL-17A cytokines in the spleen treated with CX-5461 are significantly down-regulated compared with the acute rejection group (AR), and the anti-inflammatory cytokine IL-10 is significantly up-regulated (***P<0.001).

The results show that CX-5461 may reduce the occurrence of immune rejection in transplantation, reduce the expression of related inflammatory factors and increase the expression of anti-inflammatory factors.

Figure 3A:
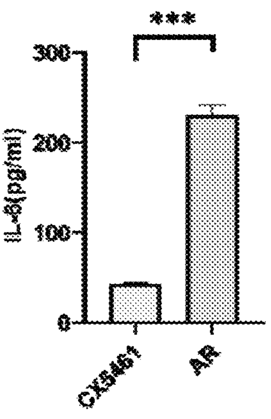
FIG. 3A shows the effect of CX-5461 on IL-6 cytokine in serum on the seventh day aft renal transplantation.
Figure 3B:
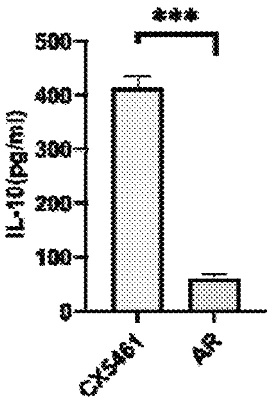
FIG. 3B shows the effect of CX-5461 on IL-10 cytokine in serum on the seventh day aft renal transplantation.

The results of the influence of cytokines in serum on the seventh day after renal transplantation are shown in FIG. 3A and FIG. 3B. It is observed that after CX-5461 treatment, compared with acute rejection group (AR), IL-6 cytokines in serum are significantly down-regulated and IL-10 cytokines are up-regulated (***P<0.001), indicating that CX-5461 may reduce ischemia-reperfusion injury and immune rejection after renal transplantation, and reduce inflammatory reaction.

Figure 4A:
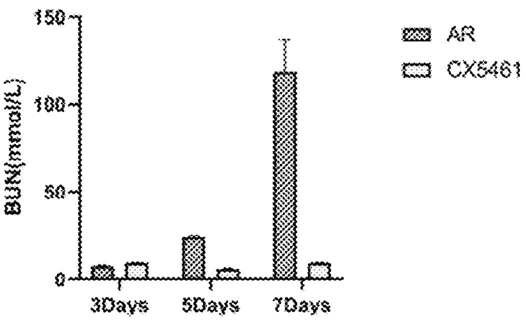
FIG. 4A illustrates the changes of creatinine on the third, fifth and seventh day after renal transplantation treated with CX-5461.
Figure 4B:
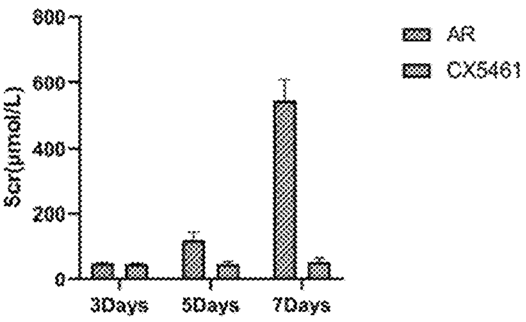
FIG. 4B illustrates the changes of urea nitrogen levels on the third, fifth and seventh day after renal transplantation treated with CX-5461.

The change results of creatinine and urea nitrogen levels on the third, fifth and seventh day after renal transplantation are shown in FIG. 4A and FIG. 4B. It is observed that the levels of creatinine and urea nitrogen remain at a low level after CX-5461 treatment, while the creatinine and urea nitrogen levels in acute rejection group (AR) continue to increase.

Figure 5A:
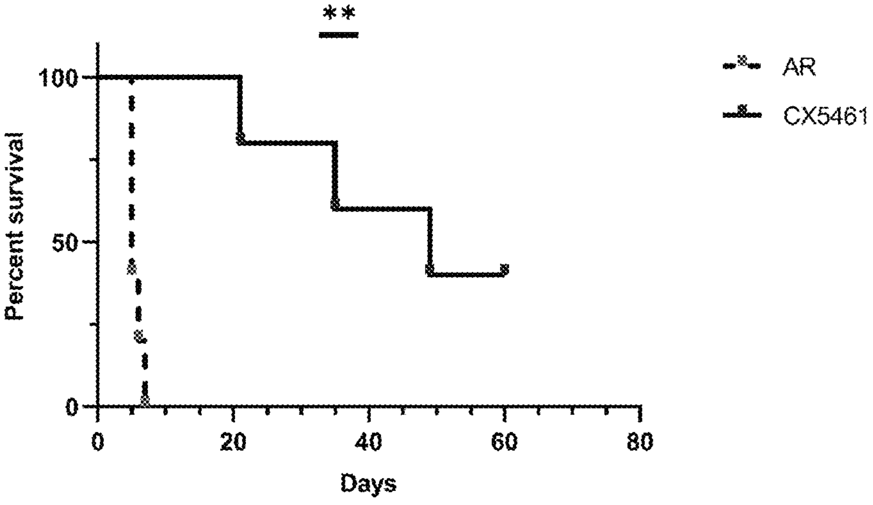
FIG. 5A shows the comparison of survival period of rats after CX-5461-treated renal transplantation in CX-5461 and AR groups.
Figure 5B:
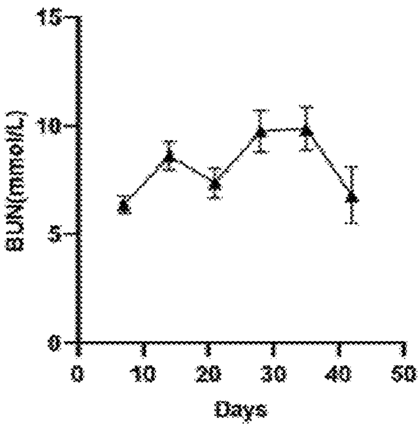
FIG. 5B shows the changes of creatinine within 42 days after CX-5461-treated renal transplantation in CX-5461 and AR groups.
Figure 5C:
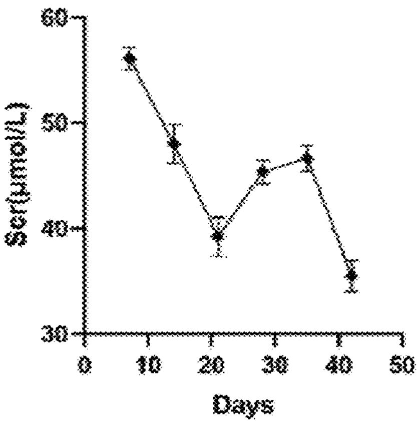
FIG. 5C shows the changes of urea nitrogen levels within 42 days after CX-5461-treated renal transplantation in CX-5461 and AR groups.

The survival time of rats after renal transplantation and the changes of creatinine and urea nitrogen levels within 42 days are shown in FIG. 5A, FIG. 5B and FIG. 5C. It can be seen that the survival time of rats after CX-5461 treatment is significantly longer than that of acute rejection group, and the creatinine and urea nitrogen levels remain at a relatively low level. It shows that CX-5461 can maintain the renal function index at a normal level and reduce the ischemia-reperfusion injury and immune rejection after renal transplantation.

Figure 6A:
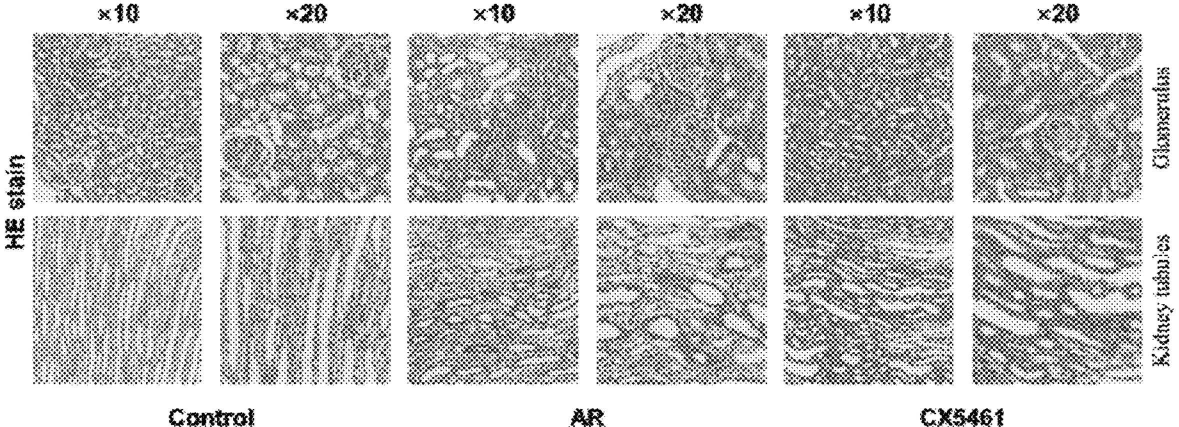
FIG. 6A shows the results of renal H&E stain on the seventh day of renal transplantation in CX-5461-treated rats.
Figure 6B:
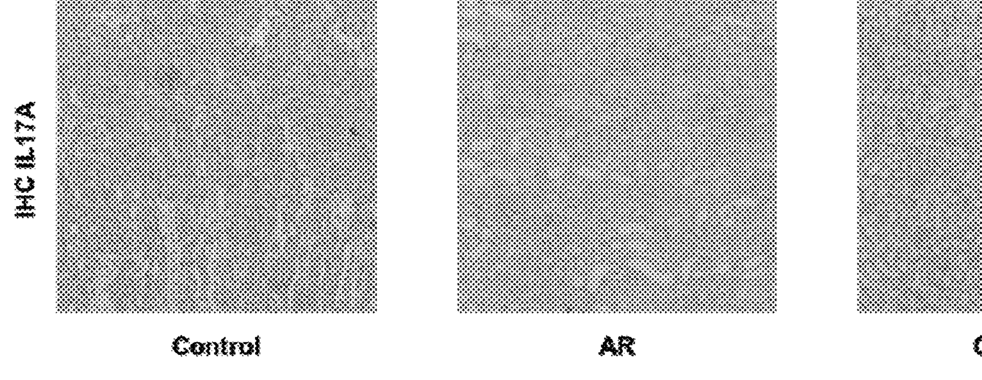
FIG. 6B shows the results of immunohistochemical stain on the seventh day of renal transplantation in CX-5461-treated rats.

On the seventh day after renal transplantation of rats, results of H&E staining and immunohistochemical staining are shown in FIG. 6A and FIG. 6B. It can be seen that the glomerulus of rats treated with CX-5461 has no obvious shrinkage, no obvious changes in renal tubules, no obvious infiltration of inflammatory cells and reduced renal fibrosis. It shows that CX-5461 can reduce ischemia-reperfusion injury and immune inflammatory reaction after renal transplantation.

Figure 7A:
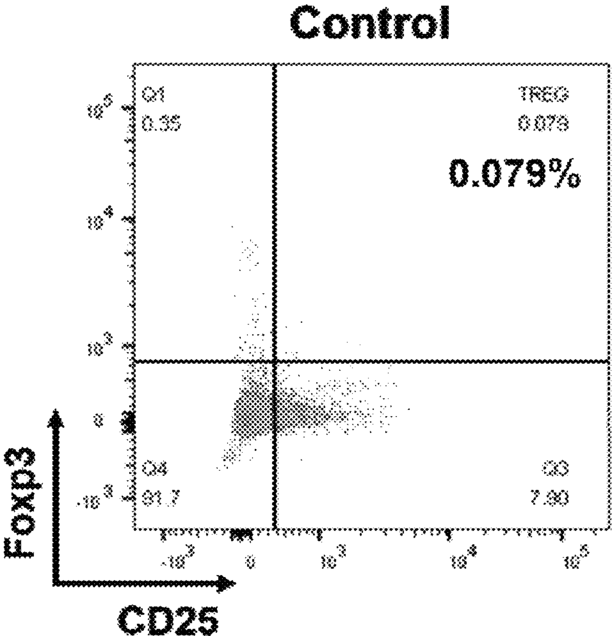
FIG. 7A shows the detection of $CD4^+$ in the spleen of rats on the seventh day after renal transplantation.
Figure 7B:
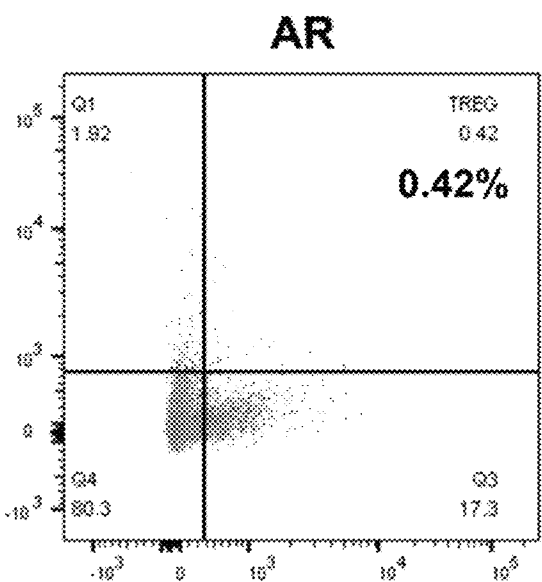
FIG. 7B shows the detection of $CD25^+$ in the spleen of rats on the seventh day after renal transplantation.
Figure 7C:
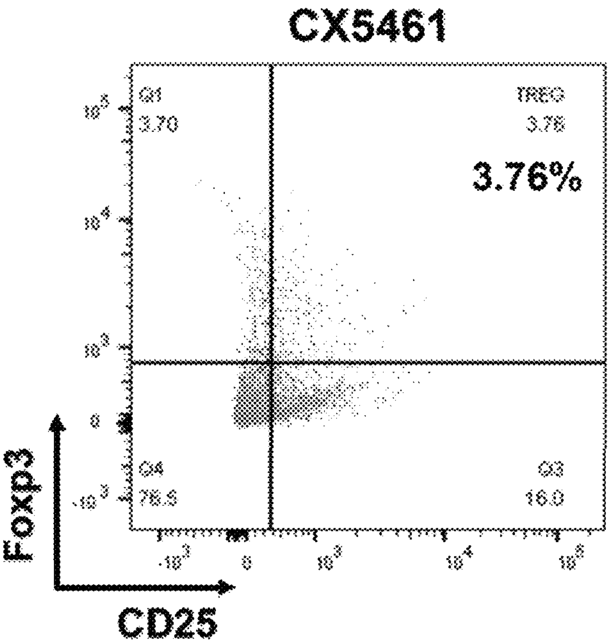
FIG. 7C shows the detection of $Foxp3^+$ in the spleen of rats on the seventh day after renal transplantation.

The detection of $CD4^+CD25^+Foxp3^+$ on the seventh day after renal transplantation in rats is shown in FIG. 7A, FIG. 7B, and FIG. 7C, and the proportion of Treg cells in the spleen of rats treated with CX-5461 is obviously increased.

The results of FIG. 1, FIG. 2A-FIG. 2C, FIG. 3A-FIG. 3B, FIG. 5A-FIG. 5C, FIG. 6A-FIG. 6B and FIG. 7A-FIG. 7C also show that CX-5461 can significantly reduce the occurrence of acute rejection in renal transplantation. The results suggest that there is no obvious inflammatory infiltration in the appearance of transplanted kidney in rats and the degree of fibrosis is low. CX-5461 is capable of reducing the levels of IL-17A cytokine in rat kidney transplantation and IL-6 cytokine in vivo, increasing the proportion of Treg cells in spleen and the level of IL-10 cytokine in anti-inflammation, prolonging the survival time of rats, and significantly reducing the occurrence of immune rejection in kidney transplantation.

In addition, the results of FIG. 2A-FIG. 2C, FIG. 3A-FIG. 3B, FIG. 4A-FIG. 4B and FIG. 6A and FIG. 6B also show that CX-5461 has the effect of preventing renal ischemia-reperfusion injury after renal transplantation. The results show that CX-5461-treated rats have no obvious shrinkage of glomerulus, no obvious changes of renal tubules, no obvious infiltration of inflammatory cells and decreased renal fibrosis, and reduced levels of creatinine and urea nitrogen in blood after renal transplantation in rats, suggesting a certain restored renal function.

To sum up, CX-5461 may obviously reduce the occurrence of acute rejection after renal transplantation and resist renal ischemia-reperfusion injury after renal transplantation, reduce the levels of creatinine and urea nitrogen in blood after renal transplantation in rats, reduce the levels of IL-17A cytokines in renal transplantation in rats and IL-6 cytokines in vivo, increase the proportion of Treg cells in spleen and the level of anti-inflammatory cytokine IL-10, prolong the survival time of rats and reduce the content of creatinine in blood, significantly prolong the long-term survival rate after renal transplantation in rats, indicating that CX-5461 may be used as a new immunosuppressant to treat renal allograft rejection, especially to inhibit acute rejection after renal transplantation, with a protective effect on renal ischemia-reperfusion injury after transplantation.

What is claimed is:
1. A method for treating an immune rejection in a patient after a renal transplantation, comprising administering to the patient in need thereof a composition comprising, as a main active ingredient, a compound of formula:
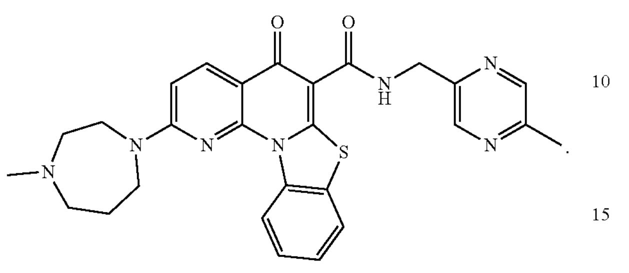
* * * * *